United States Patent [19]

Fiehler

[11] Patent Number: 4,946,601
[45] Date of Patent: Aug. 7, 1990

[54] BLOOD SERUM SEPARATOR TUBE

[75] Inventor: William R. Fiehler, St. Louis, Mo.

[73] Assignee: Sherwood Medical Company, St. Louis, Mo.

[21] Appl. No.: 235,068

[22] Filed: Aug. 22, 1988

[51] Int. Cl.⁵ ............................................. B01D 21/26
[52] U.S. Cl. ................................... 210/782; 210/516; 210/789; 422/101; 436/177; 494/37
[58] Field of Search ............... 210/514, 515, 516, 782, 210/787, 789; 422/101, 102; 436/177; 494/16, 20, 37; 435/2

[56] References Cited

U.S. PATENT DOCUMENTS

| | | | |
|---|---|---|---|
| 3,909,419 | 9/1975 | Ayres | 210/789 |
| 3,919,085 | 1/1975 | Ayres | 210/789 |
| 3,920,549 | 11/1975 | Gigliello et al. | 210/516 |
| 4,021,340 | 5/1977 | Zine, Jr. | 210/789 |
| 4,046,699 | 9/1977 | Zine, Jr. | 210/789 |
| 4,055,501 | 10/1977 | Cornell | 210/789 |
| 4,101,422 | 7/1978 | Lamont et al. | 210/789 |
| 4,148,764 | 4/1979 | Lamont et al. | 210/789 |
| 4,235,725 | 11/1980 | Semersky | 210/516 |
| 4,246,123 | 1/1981 | Cornell et al. | 210/515 |
| 4,386,003 | 5/1983 | Fiehler | 210/516 |
| 4,426,290 | 1/1984 | Ichikawa et al. | 210/789 |
| 4,569,764 | 2/1986 | Satchell | 210/516 |
| 4,816,168 | 3/1989 | Carrol et al. | 210/782 |
| 4,818,418 | 4/1989 | Saunders | 210/782 |
| 4,844,818 | 7/1989 | Smith | 210/789 |
| 4,867,887 | 9/1989 | Smith | 210/789 |

Primary Examiner—W. Gary Jones
Attorney, Agent, or Firm—Andrew J. Beck; Montgomery W. Smith; Richard D. Allison

[57] ABSTRACT

In a blood serum separator tube for separating blood into a lighter phase and a heavier phase, the thixotropic gel material initially disposed in the container lower end of the tube is protected from contact with any atmosphere contained in the tube, thus preventing separation of silicone oil from the silica-silicone fluid gel material during manufacture or storage. The gel material may be microencapsulated, or contained in a smaller number of larger capsules, or a single capsule. Alternatively, the gel material may be sealed in the tube under a curable elastomeric material, or under a water soluble material which dissolves upon contact with the blood being separated.

28 Claims, 1 Drawing Sheet

BLOOD SERUM SEPARATOR TUBE

BACKGROUND OF THE INVENTION

1. Field of the Invention

This invention relates to blood serum separator tubes useful for separating the serum and red blood cell portions of a collected blood sample through centrifugation. More specifically, the invention relates to arrangements for improving the performance of thixotropic gels used as partitioning materials in such serum separator tubes.

2. Brief Description of the Prior Art

Blood collection and separating devices are known in which a collected sample of blood is added to a glass tube containing a thixotropic gel having a density between that of blood serum and red blood cells. During centrifugation, the thixotropic gel acts as a partitioning material and is displaced upwardly in the blood sample until it reaches an equilibrium point located between the blood serum or plasma and the heavier red cell portions of the blood. At equilibrium, the gel forms a chemical and mechanical barrier between the serum and the heavier coagulum. The lighter fraction can then be easily decanted directly from the upper portion of the collection tube for analysis in automated blood analyzing equipment.

FIG. 1 shows a prior art blood serum separator tube 10 including a tube 12 which may be silicone-coated glass, a stopper 14 which may be silicone-lubricated butyl rubber, and a partitioning material or gel 16 which is an inert, thixotropic material. Such apparatus is described in Gigliello, et al., U.S. Pat. No. 3,920,549 for "Method and Apparatus for Multiphase Fluid Collection and Separation," that entire disclosure hereby being incorporated by reference.

In the prior art configuration illustrated in FIG. 1, the apparatus further includes a smaller moveable cup or energizer 18 positioned inside the tube 12 and on top of the thixotropic gel 16. Furthermore, the energizer 18, which is open at its upper end 19, may contain microscopic glass particles 20 which serve to promote coagulation by providing an expanded surface area inside the tube 12 during centrifugation. In this blood serum separator tube 10, the thixotropic gel 16 is exposed to any atmosphere 22 contained in the tube 10 at an annular surface 25 around the gel energizer 18, between the energizer 18 and the inner wall 13 of the tube.

In common use, blood is drawn into the tube 12, and the glass powder 20 is suspended throughout the collected blood. Coagulation occurs for a predetermined period of time, e.g., 15 minutes, and then the tube is centrifuged for a predetermined length of time at a particular centrifugation speed, the particular speed depending upon the size of the centrifuge being used. During centrifugation, the coagulum fills the energizer 18 and drives the energizer 18 into the gel 16 at the base 15 of the tube 12, causing the gel 16 to temporarily change viscosity. The gel 16 then flows up around the sides of the energizer 18 towards a mid-portion 17 of the tube until it reaches an equilibrium point between the separated serum and coagulum. Also moving below the gel barrier with the coagulum are the glass powder particles 20.

The specific gravity of blood serum ranges from between about 1.026 and 1.031, and the specific gravity of the coagulum or clot portion ranges from between about 1.092 and 1.095. Once centrifugation is complete, the lighter serum fraction may be easily removed for further analysis, for example, in automated blood-analyzing apparatus.

A preferred thixotropic composition for use in such separator tubes is described in the inventor's own prior U.S. Pat. No. 4,386,003, for "Blood Separating Composition," the entire disclosure of which is hereby incorporated by reference. As described therein, a preferred thixotropic gel material is a silica-silicone fluid gel formed by the reaction between silicone fluid, a filler material (such as silica particles) and a thixotropic property-imparting amount of a network former. The relative amounts of the gel components are selected so as to yield a gel having a specific gravity ranging between about 1.03 and 1.09, and preferably about 1.04. Silicone fluids used to prepare such gels are conventionally characterized as "silicone oils," and the terms "silicone fluid" and "silicone oil" as used herein are interchangeable.

While silica-silicone fluid gels provide a superior chemical and physical barrier in blood serum separator tubes as described above, a known problem in the use of such gels is that oil-like films or droplets of pure silicone oil separate from the gel material at exposed surfaces of the gel material during storage. This problem is noted in Murty, U.S. Pat. 4,180,465 for "Fluid Collection Device With Phase Separation Means." Such exposed surfaces occur at the annular surface 25 between the gel energizer 18 and inner wall 13 of the tube 12. Also, bubbles formed in the gel during manufacture present the same atmospheric contact and thus also contribute to separation of silicone oils from the gel during storage. Still further, when a separator tube as shown in FIG. 1 is stored on its side, the energizer 18 may move toward or against the inner wall 13 of the tube 12 by the influence of gravity. In so moving, a capillary effect may further promote separation of silicone oil from the thixotropic gel 16.

The silicone oils are lighter in density than the formed gel barrier and therefore rise into or on top of the separated serum portion of the blood sample, toward the stopper 14. Upon being decanted along with the blood serum, such silicone oils cause clogging and fouling of automated blood analyzing apparatus.

The problem of oil separation is not unique to silicone-based thixotropic gels. The same degradation has been found to occur in many hydrocarbon-based gel compositions. Such hydrocarbon-based gels include polyester, disclosed in Kessler et al., U.S. Pat. No. 4,350,593, for "Assembly, Compositions and Method for Separating Blood"; copolyesters, disclosed in Lamont et al., U.S. Pat. No. 4,101,422, for "Copolyesters Useful In Blood Separation Assemblies", and also in Lamont et al., U.S. Pat. No. 4,148,764, for "Copolyesters Useful In Blood Separation Assemblies"; polybutene, disclosed in Zine, Jr., U.S. Pat. No. 4,021,340, for "Blood Separating Composition"; polybutadiene, disclosed in Semersky, U.S. Pat. No. 4,235,725, for "Sterile Blood-Collecting and Separating Device"; and alpha-olefin-dimaleate copolymer, disclosed in Ichikawa et al., U.S. Pat. No. 4,426,290, for "Apparatus for Separating Blood." Cornell, U.S. Pat. No. 4,055,501, for "Fluid Collection Device With Phase Partitioning Means," also discloses hydrocarbon-based materials including polybutene and polybutadiene. The entire disclosure of each of these U.S. patents is hereby expressly incorporated by reference.

In Ayres, U.S. Pat. No. 3,909,419 for "Plasma Separator With Squeezed Sealant," a blood collection and separator assembly is described, including a pair of cylinders slidably disposed in the tube. The top cylinder has a specific gravity greater than the bottom cylinder so that upon centrifugation, the cylinders will move together. Upon such movement, the cylinders rupture and squeeze out one or more layers of microencapsulated beads of gelatin or other sealant disposed therebetween. Positioning of the seal is established by selecting the average specific gravity of the top and bottom cylinders to be between that of the plasma and coagulum. The microencapsulated sealant thereby forms a seal between the cylinders and the inner wall of the tube slightly above the interface between the two phases of the blood. Proper positioning of the described seal depends on accurate mechanical operation of the dual cylinder arrangement.

Thus, the need for an improved blood serum separating tube having the benefits but not the drawbacks of the various gel materials is readily seen.

SUMMARY OF THE INVENTION

It is a broad object of the invention to provide a blood serum separator tube which conveniently and effectively separates blood serum from coagulum upon centrifugation and which does not cause clogging or fouling of automated blood analyzing equipment.

An object of the invention is to provide a blood serum separator tube which prevents separation of oils from thixotropic gel materials used therein as blood separating compositions.

Another object is to prevent separation of silicone oil from a silica-silicone fluid thixotropic gel composition used in a blood serum separator tube.

Another object is to provide an improved blood serum collection tube which is used in precisely the same manner as existing serum separator tubes.

Still another object is to increase the shelf life of blood separator tubes.

Another object of the invention is to eliminate degradation of the thixotropic gel material in a blood serum separator tube which may result from storage position, a variable wholly outside the control of the tube manufacturer.

These as well as other objects and advantages of the present invention will become apparent from the following detailed description and accompanying drawings.

DETAILED DESCRIPTION OF THE PREFERRED EMBODIMENTS

Figure 1:
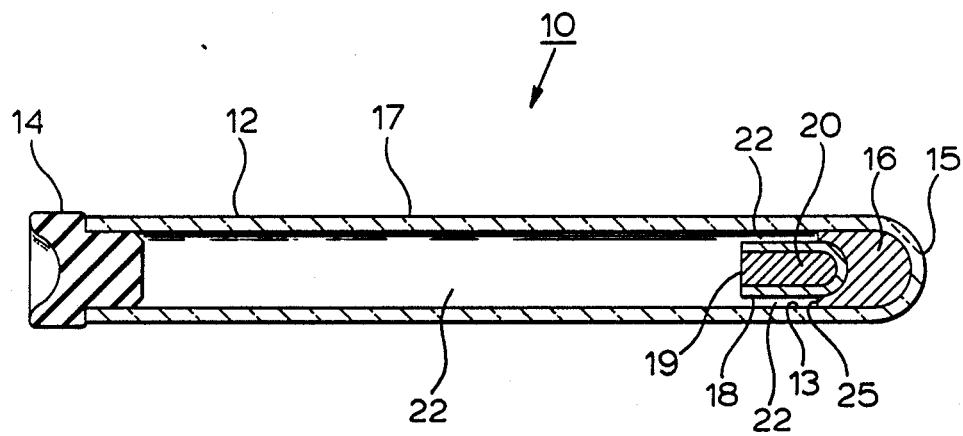
FIG. 1 is a side cross-sectional view of a prior art blood serum separator tube.
Figure 2:
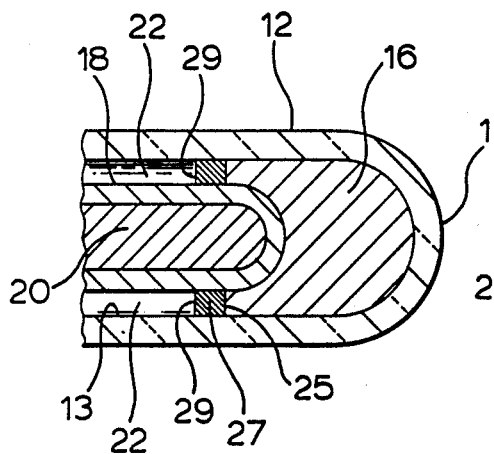
FIG. 2 is a partial side cross-sectional view of a blood separator tube according to a preferred embodiment of the present invention.

Referring now to FIG. 2, an enlarged partial side cross-sectional view of a blood separator tube according to a preferred embodiment of the present invention is shown. Where structural elements and materials are common to the prior art blood serum separator tube 10 of FIG. 1, the same reference numerals are used to identify such elements.

As described previously, an open-ended cup or energizer 18 is disposed inside the bottom end 15 of a blood separator container in the form of a tube 12. The energizer 18 is partially submerged or embedded in a thixotropic composition 16, which is preferably a silica-silicone fluid gel, in the tube 12. Because the outside diameter of the energizer 18 is smaller than the inside diameter of the tube 12, an annular surface 25 of the gel 16 is formed between the energizer 18 and the inner wall 13 of the tube 12.

To prevent the gel surface 25 from contacting any atmosphere 22 contained in the tube 12, there is added a sealing material 27 over the gel 16 and around the energizer 18. The sealant is preferably a curable liquid elastomer, such as a low viscosity curable liquid silicone. An amount of filler material should be added to the liquid elastomer, if necessary, so that the cured elastomer 27 has a specific gravity at least as great as that of the thixotropic gel 16 in the tube 12, to prevent portions of the elastomer material from suspending in the lighter serum fraction after centrifugation.

The elastomer 27 may be cured at room temperature, by application of heat, or by other known methods of curing. A preferred curable silicone elastomer is marketed by Dow-Corning Co. (Midland, Mich.) under the designation "Q72218". This is a two-part system comprising a silicone base and catalyst. A presently preferred filler material for use with this elastomer is hydrophobic silica. One such commercially available material is marketed by DeGussa Corp. (Arlington Heights, Ill.) under the designation "D-17".

The components of the curable silicone elastomer 27 are first mixed and degassed according to known techniques. With the tube 12 held vertically, an amount of low viscosity liquid silicone, including the filler, is dispensed onto the top of the thixotropic gel 16. The energizer 18 is then dropped onto the liquid silicone, forcing the silicone liquid upwardly around the energizer 18. The amount dispensed is sufficient to fill the space between the energizer 18 and the inner wall 13 of the tube 12, preferably without reaching the open end 19 of the energizer 18. The elastomer 27 is then cured, bonding the energizer 18, which may be a polypropylene cup, to the tube inner wall 13.

The height of the cured elastomer seal 29 and the strength of the cured elastomer determine the force necessary to tear the seal 29 upon centrifugation. The optimum amount of liquid silicone and the optimum silicone base/catalyst ratio (which determines strength characteristics of the cured silicone) will depend upon the specific dimensions of the separator tube and energizer, and may be readily determined without undue experimentation to suit the user's particular needs. For the blood serum separator tube marketed by Sherwood Medical (St. Louis, Mo.) under the designation "COR-VAC", 10 mL style, the presently preferred silicone base/catalyst ratio for Dow-Corning "Q72218" curable silicone is 1.0:0.8, the amount of filler to be added is 16 parts per hundred (pph), and the presently preferred amount of the mixture to be dispensed into the tube is 120 microliters. The elastomer 27 is then cured at room temperature for approximately twenty-four (24) hours, according to the presently preferred embodiment of the invention.

In use, when the separator tube so prepared is centrifuged, movement of the energizer 18 tears the cured seal 29, thus allowing mixing and then migration of the silica-silicone fluid gel 16 to its appropriate sealing position. Because the elastomer specific gravity has been specially selected, the torn fragments of the seal 29 will lodge in the thixotropic gel barrier, or below the barrier in the coagulum.

Alternatively, a water soluble polymer such as PVP (polyvinylpyrrolidone) may be substituted for the more brittle curable elastomer 27. The water soluble polymer is then dissolved upon contact with the collected blood sample, thus releasing the thixotropic gel form its protected enclosure. The specific gravity of the polymer, after being dissolved, is again specially selected so as to migrate to a level coincident with or below the thixotropic gel barrier.

One problem not addressed by the aforementioned preferred embodiment is the unwanted presence of bubbles in the silica-silicone fluid gel. Such bubbles present exposed contact surfaces at which oil, such as silicone oil, may tend to separate from the thixotropic gel during storage over time. It has been observed that oil separation is a function of exposed surface area of the silica-silicone fluid gel material.

Figure 3:
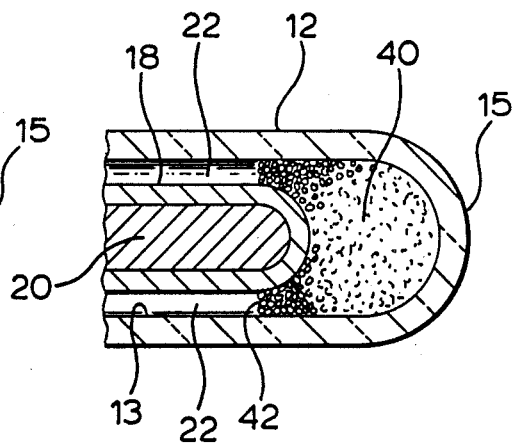
FIG. 3 is a partial side cross-sectional view of a blood separator tube according to another preferred embodiment of the invention.

A preferred embodiment directed toward eliminating the presence of such bubbles altogether is shown in FIG. 3, in which the customary tube 12 has disposed in its bottom end 15 an amount of thixotropic gel material 40. Partially embedded in the upper portion of the gel material 40 is the energizer 18, which may be filed with coagulation enhancing glass particles 20. The gel material 40 is exposed at the upper annular surface 42 thereof, between the energizer 18 and the inner wall 13 of the tube 12, to any atmosphere 22 contained in the tube 12.

In the blood serum separator tube of FIG. 3, the thixotropic silica-silicone fluid gel material is microencapsulated in microcapsules having sufficiently strong walls of encapsulating material so as to prevent premature rupturing before centrifugation, yet still sufficiently fragile so as to rupture during centrifugation. Alternatively, the gel mass may be encapsulated in a single capsule prior to insertion into the tube 12. Capsule sizes ranging between microcapsules and a single capsule are also possible.

Suitable encapsulating materials include polymers such as styrene or water insoluble polyacrylates. These materials form a brittle capsule wall which rupture during centrifugation Alternatively, water soluble encapsulating materials may be employed, such as PVP (polyvinylpyrrolidone), polyacrylic acid or similar polymers. Such water soluble capsules dissolve on contact with the collected blood sample, thus releasing the thixotropic gel to perform its serum separating function.

Numerous variations and modifications, in addition to those already described, will be plain to those skilled in the art. For example, solid beads of encapsulant may be interspersed in the bottom of the tube 12 of FIG. 3, in addition to the thixotropic gel microcapsules. By adjusting the specific gravity of the beads to that of the silica-silicone fluid gel material, the beads form a solid physical serum barrier upon centrifugation, the interstices between the beads being filled in by the thixotropic gel.

The invention is limited only by the appended claims.

I claim:

1. A fluid separator apparatus for separating blood into a lighter phase and a heavier phase comprising:
    a container;
    a gel material disposed in the container, said gel material being thixotropic and chemically inert to the lighter and heavier phases and having a specific gravity intermediate the specific gravities of the heavier and lighter phases; and
    a curable sealing means having a specific gravity at least as great as the specific gravity of said gel material and wherein said sealing means is curable in said container and is in contact with said gel material for sealing said gel material from any atmosphere in said container.

2. A fluid separator apparatus for separating blood into a lighter phase and a heavier phase comprising:
    a container having an upper end and a lower end;
    a gel material disposed in the lower end of said container, said gel material being thixotropic and chemically inert to the lighter and heavier phases and having a specific gravity intermediate the specific gravities of the heavier and lighter phases;
    a sealing means having a specific gravity greater than the gel material and wherein said sealing means is in contact with said gel material for sealing said gel material from any atmosphere in said container;
    an energizer means, having a lower portion in contact with said gel material for causing said gel material to flow toward said upper end of said container upon application of centrifugal force to said container and in response to movement of said energizer means toward said lower end of said container, and
    wherein said sealing means is cured in said container and contacts an outer surface on said energizer means and an inner surface on said container.

3. The apparatus of claim 2, wherein said sealing means initially bonds said energizer means to the inner wall of said container, and wherein the bond of said sealing means with the inner wall of said container is broken, upon the movement of said energizer means during application of centrifugal force to said container.

4. The apparatus of claims, 1, 2 or 3, wherein said gel material is partially formed from a material selected from the group consisting of silicone oil, polyester, copolyester, polybutene, polybutadiene and alpha-olefine-dimaleate copolymer and wherein said sealing means includes a filler material therein.

5. The apparatus of claim 4, wherein said sealing means comprises an elastomer which is curable and is positioned between said gel material and any atmosphere in said container.

6. The apparatus of claim 5, wherein said elastomer is initially a low viscosity silicone liquid which is chemically inert to the lighter phase of the blood.

7. The apparatus of claim 5, wherein said elastomer is adapted to be cured by the passage of time.

8. The apparatus of claim 5, wherein said elastomer is adapted to be cured by the application of heat thereto.

9. The apparatus of claim 4, wherein said sealing means is a water soluble material which is adapted to dissolve on contact with blood.

10. The apparatus of claim 9, wherein said water soluble material is selected from the group consisting of polyvinylpyrrolidone, and polyacrylic acid.

11. A fluid separator apparatus for separating blood into a lighter phase and a heavier phase comprising:
    a container having an upper end and a lower end;
    a gel material disposed in the lower end of said container, said gel material being thixotropic and chemically inert to the lighter and heavier phases and having a specific gravity intermediate the specific gravities of the heavier and lighter phases;
a sealing means in contact with said gel material for sealing said gel material being thixotropic and chemically inert to the lighter and heavier phases and having a specific gravity intermediate the specific gravities of the heavier and lighter phases;
a sealing means in contact with said gel material for sealing said gel material from any atmosphere in said container;
an energizer means, having a lower portion in contact with said gel material for causing said gel material to flow toward said upper and of said container upon application of centrifugal force to said container and in response to movement of said energizer means toward said lower end of said container;
wherein said sealing means also contacts an outer surface on said energizer means and an inner surface on said container, and
wherein the sealing means comprises at least one capsule of a capsule wall material encapsulating the gel material therein.

12. The apparatus of claim 11, wherein the gel material is partially formed from a material selected from the group consisting of silicone oil, polyester, copolyester, polybutene, polybutadiene and alpha-olefin-dimaleate copolymer.

13. The apparatus of claim 11, wherein the sealing means comprises microcapsules.

14. The apparatus of claim 11, wherein the capsule wall comprises a brittle material so as to rupture upon application of centrifugal force.

15. The apparatus of claim 11, wherein the capsule wall comprises a water soluble material so as to dissolve upon contact with blood.

16. The apparatus of claim 15, wherein the water soluble material is selected from the group consisting of polyvinylpyrrolidone and polyacrylic acid.

17. A method of making a fluid separator apparatus including a gel for separating blood into a lighter phase and a heavier phase in a container, the method comprising the steps of:
providing a container having an upper end and a lower end;
depositing in the container an amount of gel material, the gel material being thixotropic and chemically inert to the lighter and heavier phases and having a specific gravity intermediate the specific gravities of the heavier and lighter phases;
pouring and subsequently curing a liquid sealing means having a specific gravity at least as great as the specific gravity of the gel material into the lower end of the container, in contact with the gel material, in an amount sufficient to prevent contact between the gel material and any atmosphere in the container.

18. The method of claim 17, wherein the gel material is partially formed from a material selected from the group consisting of silicone oil, polyester, copolyester, polybutene, polybutadine, and alpha-olefin-dimaleate copolymer.

19. A method of making a fluid separator apparatus including a gel for separating blood into a lighter phase and a heavier phase in a container, the method comprising the steps of:
providing a container having an upper end and a lower end;
depositing in the container an amount of gel material, the gel material being thixotropic and chemically inert to the lighter and heavier phases and having a specific gravity intermediate the specific gravities of the heavier and lighter phases;
depositing in the container, in contact with the gel material, an amount of a sealing means having a specific gravity at least as great as the specific gravity of the gel material for preventing contact between the gel material and any atmosphere in the container;
after depositing the sealing means in the container, placing a lower portion of an energizer means for causing the gel material to flow toward the container upper end under the influence of centrifugal force, on top of the sealing means;
permitting the sealing means to flow upwardly around the energizer means to seal a space between a container inner wall and the energizer means, and
curing said sealing means to create a barrier between said gel material and the atmosphere in said container.

20. The method of claims 17 or 19, wherein the sealing means comprises a tearable and curable elastomer and comprising the further step of curing the sealing means after said sealing means has been deposited in said container so that the sealing means may be torn by the application of centrifugal force to the container.

21. The method of claim 19, wherein the curable elastomer is a low viscosity silicone liquid.

22. The method of claims 17 or 19, wherein said sealing means comprises a water soluble material particularly adapted to dissolve upon contact with blood.

23. A method of making a fluid separator apparatus for separating blood into a lighter phase and a heavier phase comprising the steps of:
providing a container having an upper end and a lower end;
depositing in said container an amount of gel material, the gel material being thixotropic and chemically insert to said lighter and heavier phases and having a specific gravity intermediate said specific gravities of said heavier and lighter phases;
depositing in the container, in contact with the gel material, an amount of a water soluble material comprising a sealing means for preventing contact between the gel material and any atmosphere in the container and which dissolves on contact with blood; and wherein the water soluble material is selected from the group consisting of polyvinylpyrrolidone and polyacrylic acid.

24. A method of separating blood into a lighter phase and a heavier phase comprising the steps of:
providing a container having an upper end and a lower end, gel material initially disposed in the container lower end, the gel material being thixotropic and chemically inert to the lighter and heavier phases and having a specific gravity intermediate the specific gravities of the heavier and lighter phases, the container having energizer means having a lower portion initially partially submerged the gel material for causing the gel material to flow toward the container upper end, under the influence of centrifugal force, along an inner wall of the container in a space between the inner wall and the energizer means, in response to movement of the energizer means toward the container lower end, and pouring a curable searing means having a specific gravity at least as great as the specific gravity of the gel material initially on top of the gel material in the space between the inner wall and the energizer means for preventing contact between the gel and any atmosphere in the upper end of the container;

placing an amount of blood to be separated in the container after the sealing means has been cured; and centrifuging the container so as to cause movement of the energizer means toward the lower end of the container, thus breaking the cured sealing means and causing the gel material to migrate in the blood toward the upper end of the container to a location intermediate the lighter phase and the heavier phase.

25. A method of separating blood into a lighter phase and a heavier phase comprising the steps of:

providing a container having an upper end and a lower end, encapsulated gel material initially disposed in the container lower end, the gel material being thixotropic and chemically inert to the lighter and heavier phases and having a specific gravity intermediate the specific gravities of the heavier and lighter phases, the gel material being encapsulated in a brittle capsule wall material, the container having energizer means having a lower portion initially partially submerged in the gel material for causing the gel material to flow toward the container upper end, under the influence of centrifugal force, along an inner wall of the container in a space between the inner wall and the energizer means, in response to movement of the energizer means toward the container lower end;

centrifuging the container so as to cause movement of the energizer means toward the container lower end, causing the brittle capsule wall material to rupture and release the encapsulated gel material, permitting the gel material to migrate in the blood toward the container upper end to a point intermediate the lighter phase and the heavier phase.

26. A fluid separator apparatus including a thixotropic gel for separating blood into a lighter phase and a heavier phase of blood in a container, the method comprising:

a container having an upper end and a lower end;

a gel material disposed in the lower end of said container, the gel material being thixotropic and chemically inert to the lighter and heavier phases and having a specific gravity intermediate the specific gravities of the heavier and lighter phases;

a sealing means in contact with the gel material for substantially sealing the gel material from atmosphere in the container and wherein said sealing means has a specific gravity at least as great as the specific gravity of said gel material;

an energizer means having a lower portion in contact with the gel material and an upper portion in contact with the atmosphere in the container and wherein the energizer means causes said gel material to flow toward the upper end of the container upon application of centrifugal force to the container in response to movement of the energizer means toward the lower end of the container, and wherein the sealing means forms a tearable seal between an outer surface on the energizer means and an inner surface on the container which is torn by the application of centrifugal force to the container.

27. The apparatus of claim 26 wherein the gel material is partially formed from a material selected from the group consisting of silicone oil, polyester, copolyester, polybutene, polybutadiene and alpha-olefin-dimaleate copolymer.

28. A fluid separator apparatus for separating blood into a lighter phase and a heavier phase comprising:

a container having an upper end and a lower end;

a thixotropic gel material disposed in the lower end of said container and being chemically inert to the lighter and heavier phases of the separated blood and having a specific gravity intermediate the heavier and lighter phases of the separated blood;

a sealing means in contact with said gel material for substantially sealing said gel material from atmosphere in said container and wherein said sealing means is chemically inert with the lighter phase and has a specific gravity greater than the specific gravity of the gel material;

an energizer means having a lower portion in contact with said gel material for causing said gel material to flow toward said upper end of said container upon the application of centrifugal force to said container and in response to movement of said energizer means toward said lower end of said container, and wherein said sealing means also contacts an outer surface on said energizer means and an inner surface on said container to form a tearable barrier therebetween upon the application of centrifugal force to said container.

* * * * *